(12) United States Patent
Hori et al.

(10) Patent No.: US 7,619,125 B2
(45) Date of Patent: Nov. 17, 2009

(54) HYDROGENATION PROMOTER, HYDROGENATION CATALYST, AND PROCESS FOR PRODUCING ALKENE COMPOUND

(75) Inventors: Junichi Hori, Soka (JP); Kunihiko Murata, Koshigaya (JP); Nobuhito Kurono, Sapporo (JP); Takeshi Ohkuma, Sapporo (JP); Ryoji Noyori, Tokyo (JP)

(73) Assignees: Kanto Kagaku Kabushiki Kaisha, Tokyo (JP); Nagoya Industrial Science Research Institute, Nagoya (JP)

( * ) Notice: Subject to any disclaimer, the term of this patent is extended or adjusted under 35 U.S.C. 154(b) by 353 days.

(21) Appl. No.: 11/547,002

(22) PCT Filed: Mar. 30, 2005

(86) PCT No.: PCT/JP2005/006694

§ 371 (c)(1),
(2), (4) Date: Nov. 3, 2006

(87) PCT Pub. No.: WO2005/094993

PCT Pub. Date: Oct. 13, 2005

(65) Prior Publication Data

US 2008/0033221 A1    Feb. 7, 2008

(30) Foreign Application Priority Data

Mar. 31, 2004  (JP) ............................. 2004-105517

(51) Int. Cl.
*B01J 31/00* (2006.01)
(52) U.S. Cl. ...................... 585/273; 585/271; 585/272; 502/325; 502/339
(58) Field of Classification Search ................ 502/325, 502/339; 585/271–273
See application file for complete search history.

(56) References Cited

U.S. PATENT DOCUMENTS

| 4,324,800 | A | * | 4/1982 | Umino et al. | ............... 514/534 |
| 6,150,545 | A | * | 11/2000 | Harada et al. | ............... 556/112 |
| 6,197,720 | B1 | * | 3/2001 | Heineke et al. | ............. 502/325 |

FOREIGN PATENT DOCUMENTS

| JP | A 9-313936 | 12/1997 |
| JP | A 2001-278823 | 10/2001 |
| JP | A 2003-236386 | 8/2003 |

OTHER PUBLICATIONS

Beck, A. et al. (2003). "Chapter 5. Roadmap to new catalyst system: Palladium nanoparticles," in Nanotechnology in catalysis. Edited by B. Zhou, S. Hermans, & G.A. Somorjai, Springer, 555 pgs. (cited pp. 83-110).*
Zhan, X. et al. (2001). Journal of Molecular Catalysis A: Chemical, 169, 63-66.*
A. Mastalir et al., "Preparation of Organophilic Pd-Montmorillonite, An Efficient Catalyst in Alkyne Semihydrogenation," Journal of Catalysts 194, 2000, pp. 146-152.
K. Okamoto et al., "Formation of Nanoarchitectures Including Subnanometer Palladium Clusters and Their Use as Highly Active Catalysts," J. Am. Chem. Soc., vol. 127, No. 7, 2005, pp. 2125-2135.

* cited by examiner

*Primary Examiner*—Robert J Hill, Jr.
*Assistant Examiner*—Brian McCaig
(74) *Attorney, Agent, or Firm*—Oliff & Berridge, PLC

(57) ABSTRACT

A hydrogenation promoter of the present invention is produced by reacting an alkyne compound or an alkene compound, a palladium compound represented by a general formula $Pd(II)X_jL_k$ (where L represents a monodentate ligand or a polydendate ligand other than a phosphorus-containing ligand (when two or more Ls are present in the compound, the Ls may be the same or different), X represents an anionic group, j represents a value determined according to the valence of X so that $X_j$ has a valence of −2 as a whole, and k represents an integer in the range of 0 to 4), and a base in an organic solvent. Specifically, The hydrogenation promoter of the invention includes palladium nanoparticles containing the alkyne compound or the alkene compound as an agglomeration-preventing agent.

4 Claims, No Drawings

HYDROGENATION PROMOTER, HYDROGENATION CATALYST, AND PROCESS FOR PRODUCING ALKENE COMPOUND

TECHNICAL FIELD

The present invention relates to a hydrogenation catalyst for partially hydrogenating an alkyne compound to an alkene compound, and a process for producing an alkene compound in the presence of the hydrogenation catalyst.

BACKGROUND ART

As regards a partial hydrogenation reaction for producing an alkene compound from an alkyne compound, studies using a catalyst of a transition metal such as palladium or nickel have been conducted. For example, H. Lindlar reported that an alkyne compound was partially hydrogenated in the presence of a catalyst prepared by poisoning palladium carried on calcium carbonate with lead acetate to produce a cis-alkene compound with high selectivity. At present, this catalyst is most widely used as a catalyst combining a high activity and high cis-selectivity.

The present inventors have disclosed that some phosphine-palladium complexes are useful as catalysts for partially hydrogenating alkyne compounds with high activity. For example, Patent Document 1 discloses a process of producing an alkene compound including partially hydrogenating an alkyne compound, which is a reaction substrate, using a catalytic amount of 1,2-bis(diphenylphosphino)propane palladium chloride as a phosphine-palladium complex in a mixed solvent of N,N-dimethylformamide (DMF) and an alcohol in the presence of potassium tert-butoxide or sodium borohydride and in the presence of hydrogen (for example, Japanese Unexamined Patent Application Publication No. 2003-236386).

Furthermore, in Journal of Catalysis, Vol. 194, pp. 146-152 (2000), a hydrogenation reaction of an alkyne compound using palladium nanoparticles carried on montmorillonite as a catalyst has been reported. Specifically, the following example has been reported: A hydrogenation reaction of 1-phenyl-1-butyne was conducted using the above palladium nanoparticles as a catalyst at room temperature in THF. As a result, at a reaction time of 60 minutes, 1-phenyl-cis-butene was produced in an amount of about 60%, 1-phenyl-trans-butene was produced in an amount of about 30%, and 1-phenylbutane was produced in an amount of about 10%.

DISCLOSURE OF INVENTION

The phosphine-palladium complex described in Japanese Unexamined Patent Application Publication No. 2003-236386 provides a high reaction rate as a hydrogenation catalyst and high selectivity for a cis-alkene compound when an internal alkyne compound is hydrogenated. However, to develop a hydrogenation catalyst superior to such an excellent phosphine-palladium complex is extremely useful, for example, for synthesizing medicines, agricultural chemicals, and intermediates thereof. Therefore, such a development is strongly desired in industries relating to chemicals.

On the other hand, the above-described palladium nanoparticles carried on montmorillonite can hydrogenate alkyne compounds but are disadvantageous in that it is difficult to produce cis-alkene compounds with high selectivity using the catalyst. That is, the generation of trans-alkene compounds and the generation of alkane compounds due to excessive hydrogenation cannot be effectively suppressed.

The present invention has been conceived in view of the above problems, and an object of the present invention is to provide a hydrogenation promoter and a hydrogenation catalyst that can be used to conduct hydrogenation reaction at a very high rate using a trace amount thereof. It is another object of the present invention to provide a process for producing an alkene compound using the hydrogenation promoter or the hydrogenation catalyst, in particular, to provide a process for producing a cis-alkene compound at a high rate and with high selectivity from an alkyne compound.

As described above, in Japanese Unexamined Patent Application Publication No. 2003-236386, the present inventors developed a hydrogenation catalyst including a divalent palladium complex having diphosphine as a ligand, and a base such as potassium tert-butoxide. Thereafter, the present inventors conducted intensive studies in order to develop a homogeneous palladium catalyst with a higher efficiency, and newly found a novel excellent hydrogenation catalyst that can be used to conduct hydrogenation reaction at a very high rate and that functions even when used in a trace amount, and a hydrogenation promoter that constitutes the hydrogenation catalyst and that has a function of promoting hydrogenation even when used alone. These findings led to the completion of the present invention. Furthermore, the present inventors elucidated the fact that this hydrogenation promoter is composed of palladium nanoparticles.

A hydrogenation promoter of the present invention is produced by reacting an alkyne compound or an alkene compound, at least one palladium compound selected from the group consisting of palladium compounds represented by general formulae (1) to (4) or at least one multimer thereof, and a base in an organic solvent:

$$Pd(II)X_jL_k \quad (1)$$

$$\text{a salt of } (Pd(II)X_m)^{2-} \quad (2)$$

$$\text{a salt of } (Pd(II)L_n)^{2+} \quad (3)$$

$$\text{a salt of } (Pd(IV)X_p)^{2-} \quad (4)$$

(in general formulae (1) to (4), L represents a monodentate ligand or a polydendate ligand other than a phosphorus-containing ligand (when two or more Ls are present in the compound, the Ls may be the same or different), X represents an anionic group, j represents a value determined according to the valence of X so that $X_j$ has a valence of −2 as a whole, k represents an integer in the range of 0 to 4, m represents a value determined according to the valence of X so that $X_m$ has a valence of −4 as a whole, n represents an integer in the range of 4 to 6, and p represents a value determined according to the valence of X so that $X_p$ has a valence of −6 as a whole.)

It is evident that the hydrogenation promoter of the present invention is composed of palladium nanoparticles. These palladium nanoparticles contain the alkyne compound or the alkene compound as an agglomeration-preventing agent that prevents the particles from agglomerating. The average crystal diameter of the palladium nanoparticles determined from the half-width of a diffraction peak obtained by X-ray diffractometry is preferably in the range of 0.5 to 5 nm. It is believed that the hydrogenation promoter of the present invention is produced by way of the following reaction process. That is, it is believed that when a compound having a low reducing power is used as the base, first, the organic solvent is reacted with the base to produce a reducing agent, and at least one palladium compound selected from the group consisting of palladium compounds represented by general formulae (1) to (4) or at least one multimer thereof is then reduced by the reducing agent to produce palladium nanoparticles. It is believed that, for example, when DMF is used as the organic solvent and tert-BuOK is used as the base, first, both are reacted to produce potassium formate, which is a reducing agent, in the reaction system, and the divalent to tetravalent palladium compounds are reduced by this potassium formate. It is believed that when a compound having a high reducing power is used as the base, at least one palladium compound selected from the group consisting of palladium compounds represented by general formulae (1) to (4) or at least one multimer thereof is reduced by the reducing agent to produce palladium nanoparticles.

A hydrogenation promoter of the present invention is produced by reacting an alkynyl alcohol compound or an alkenyl alcohol compound with at least one palladium compound selected from the group consisting of palladium compounds represented by general formulae (1) to (4) or at least one multimer thereof in an organic solvent. When an alkynyl alcohol compound is used as the alkyne compound, or an alkenyl alcohol compound is used as the alkene compound, a base is not essential for producing the hydrogenation promoter. It is evident that the hydrogenation promoter thus obtained is also composed of palladium nanoparticles. These palladium nanoparticles contain the alkynyl alcohol compound or the alkenyl alcohol compound as an agglomeration-preventing agent. The average crystal diameter of the palladium nanoparticles determined from the half-width of a diffraction peak obtained by X-ray diffractometry is preferably in the range of 0.5 to 5 nm.

For the purpose of this description, the term "alkyne compound" is used as a broader term including alkynyl alcohol compounds, and term "alkene compound" is used as a broader term including alkenyl alcohol compounds.

The hydrogenation promoter of the present invention functions as a hydrogenation catalyst that can be used to conduct partial hydrogenation reactions from an alkyne compound to an alkene compound when used in combination with a base and/or a reducing agent. This hydrogenation catalyst can be used to conduct these hydrogenation reactions at a very high rate using a trace amount thereof, compared with known hydrogenation catalysts. Although the hydrogenation promoter of the present invention can be used alone to conduct these hydrogenation reactions, the hydrogenation promoter of the present invention is preferably used as a hydrogenation catalyst in combination with a base and/or a reducing agent. Specifically, in general, when an internal alkyne compound is used as a reaction substrate, a trans-alkene compound is produced by isomerization or an alkane compound is produced by excessive hydrogenation reaction. Thus, it is difficult to produce a cis-alkene compound with high selectivity. In contrast, when the hydrogenation promoter of the present invention is used as a hydrogenation catalyst in combination with a base and/or a reducing agent, the hydrogenation reaction from the internal alkyne compound to the cis-alkene compound is conducted with high selectivity. Furthermore, in general, when a terminal alkyne compound is used as a reaction substrate, an alkane compound is easily produced by excessive hydrogenation reaction. In contrast, when the hydrogenation promoter of the present invention is used as a hydrogenation catalyst in combination with a base and/or a reducing agent, the hydrogenation reaction from the terminal alkyne compound to an alkene compound is conducted with high selectivity.

As described above, the hydrogenation promoter of the present invention (i.e., palladium nanoparticles containing an alkyne compound or an alkene compound as an agglomeration-preventing agent) may be used as a hydrogenation catalyst in combination with a base and/or a reducing agent. Alternatively, instead of the hydrogenation promoter of the present invention, existing palladium nanoparticles synthesized by a known process may be used as the hydrogenation catalyst. For example, known documents such as J. Am. Chem. Soc., Vol. 127 (7), pp. 2125-2135 (2005) describe a process of synthesizing palladium nanoparticles including a reaction of a divalent palladium compound with a reducing agent.

The hydrogenation promoter of the present invention preferably has the following property: When the hydrogenation promoter is used as a hydrogenation catalyst or a component of a hydrogenation catalyst, the turnover number (TON) in a hydrogenation reaction of 4-octyne is 1,000,000 or more, or the turnover frequency (TOF) at the time of the completion of the hydrogenation reaction is 100 $sec^{-1}$ or more. Herein, the term "TON" means the number of times one catalyst molecule acts on a substrate in a catalytic reaction, and is an index representing a lifetime efficiency of the catalyst. This property of a TON of 1,000,000 or more indicates a high lifetime, which cannot be achieved by known hydrogenation catalysts. The term "TOF" means a frequency at which one catalyst molecule acts on a substrate per second, and is an index representing a rate performance of the catalyst. This property of a TOF of 100 $sec^{-1}$ or more also indicates a high catalytic activity, which cannot be achieved by known hydrogenation catalysts.

A feature of the hydrogenation promoter of the present invention is that the agglomeration-preventing agent of palladium nanoparticles is an alkyne compound or an alkene compound. The coordination ability of these compounds to palladium is weaker than that of other agglomeration-preventing agents. In particular, the coordination ability of alkene compounds is weak. It is believed that, for example, when an alkyne compound is added in the preparation of the hydrogenation promoter of the present invention, the alkyne compound covers the surfaces of the palladium nanoparticles constituting the hydrogenation promoter, a part of the alkyne compound reacts with palladium to produce an alkene compound by cyclization or polymerization, and a part of the alkene compound covers the surfaces of the palladium nanoparticles together with the alkyne compound. It is believed that since a large amount of the alkyne compound, which is a substrate, is present in the hydrogenation reaction system, the substrate alkyne immediately coordinates to the palladium nanoparticles and is hydrogenated and eliminated as an alkene, thus again providing highly active palladium nanoparticles. It is believed that, according to the above mechanism, the palladium nanoparticles that are the hydrogenation promoter of the present invention exhibit a catalytic performance having a high activity and a high rate compared with known palladium nanoparticles.

Both polar solvents and nonpolar solvents can be used as an organic solvent in the reaction for producing the hydrogenation promoter, but polar solvents are preferred. Examples of polar solvents include amide solvents, ether solvents, alcohol solvents, sulfur-containing solvents, and mixtures thereof. When a base is used in the reaction for producing the hydrogenation promoter, solvents that react with the base to produce a reducing agent are preferred. For example, amide solvents are preferred. Examples of amide solvents include N-methylformamide, N,N-dimethylformamide (DMF), N-methylacetamide, and N,N-dimethylacetamide (DMA). Among these, DMF or DMA is preferred. Examples of ether solvents include tetrahydrofuran (THF) and dioxane.

Examples of alcohol solvents include methanol, ethanol, n-propanol, isopropyl alcohol (IPA), n-butanol, sec-butanol, and tert-butanol. Examples of sulfur-containing solvents include dimethyl sulfoxide (DMSO). Examples of mixed solvents include mixed solvents of an amide solvent and an alcohol solvent. The amount of the solvent used is not particularly limited and is approximately in the range of 1 to 1,000 liters per mole of palladium, and preferably in the range of 10 to 100 liters.

As regards alkyne compounds and alkene compounds that can be used in the reaction for producing the hydrogenation promoter, alkyne compounds are preferred. Among these, internal alkyne compounds are particularly preferred. From the standpoint that these compounds are dissolved in an organic solvent, these compounds are preferably a liquid at room temperature. When alkene compounds or terminal alkyne compounds are used, the reaction is not satisfactorily proceed in some cases. Specific examples of the alkyne compounds include hydrocarbon alkynes such as 2-butyne, 2-pentyne, 2-hexyne, 3-hexyne, 2-heptyne, 3-heptyne, 2-octyne, 3-octyne, 4-octyne, diisopropylacetylene, 2-nonyne, 3-nonyne, 4-nonyne, 5-nonyne, 2-decyne, 3-decyne, 4-decyne, 5-decyne, di-tert-butylacetylene, diphenylacetylene, dibenzylacetylene, methyl-iso-propylacetylene, methyl-tert-butylacetylene, ethyl-iso-propylacetylene, ethyl-tert-butylacetylene, n-propyl-iso-propylacetylene, n-propyl-tert-butylacetylene, phenylmethylacetylene, phenylethylacetylene, phenyl-n-propylacetylene, phenyl-iso-propylacetylene, phenyl-n-butylacetylene, and phenyl-tert-butylacetylene; alkynyl alcohols such as acetylene diol, 1-propyn-1-ol, 1-propyne-1,3-diol, 2-butyn-1-ol, 2-butyne-1,4-diol, 2-pentyn-1-ol, 2-pentyn-4-ol, 2-pentyn-5-ol, 2-pentyne-1,4-diol, 2-pentyne-1,5-diol, 2-hexyn-1-ol, 2-hexyn-4-ol, 2-hexyn-5-ol, 2-hexyn-6-ol, 2-hexyne-1,4-diol, 2-hexyne-1,5-diol, 2-hexyne-1,6-diol, 3-hexyn-1-ol, 3-hexyn-2-ol, 3-hexyne-1,5-diol, 3-hexyne-1,6-diol, 3-hexyne-2,5-diol, 3-hexyne-2,6-diol, 2-heptyn-1-ol, 2-heptyn-4-ol, 2-heptyn-5-ol, 2-heptyn-6-ol, 2-heptyn-7-ol, 3-heptyn-1-ol, 3-heptyn-2-ol, 3-heptyn-5-ol, 3-heptyn-6-ol, 3-heptyn-7-ol, 2-heptyne-1,2-diol, 2-heptyne-1,5-diol, 2-heptyne-1,6-diol, 2-heptyne-1,7-diol, 2-heptyne-4,5-diol, 2-heptyne-4,6-diol, 2-heptyne-4,7-diol, 3-heptyne-1,2-diol, 3-heptyne-1,5-diol, 3-heptyne-1,6-diol, 3-heptyne-1,7-diol, 3-heptyne-2,5-diol, 3-heptyne-2,6-diol, 3-heptyne-2,7-diol, 3-heptyne-5,6-diol, 3-heptyne-5,7-diol, 3-heptyne-6,7-diol, 2-octyn-1-ol, 2-octyn-4-ol, 2-octyn-5-ol, 2-octyn-6-ol, 2-octyn-7-ol, 2-octyn-8-ol, 3-octyn-1-ol, 3-octyn-2-ol, 3-octyn-5-ol, 3-octyn-6-ol, 3-octyn-7-ol, 3-octyn-8-ol, 4-octyn-1-ol, 4-octyn-2-ol, 4-octyn-3-ol, 2-octyne-1,4-diol, 2-octyne-1,5-diol, 2-octyne-1,6-diol, 2-octyne-1,7-diol, 2-octyne-1,8-diol, 2-octyne-2,5-diol, 2-octyne-2,6-diol, 2-octyne-2,7-diol, 2-octyne-2,8-diol, 2-octyne-4,5-diol, 2-octyne-4,6-diol, 2-octyne-4,7-diol, 2-octyne-4,8-diol, 2-octyne-5,6-diol, 2-octyne-5,7-diol, 2-octyne-5,8-diol, 2-octyne-6,7-diol, 2-octyne-6,8-diol, 2-octyne-7,8-diol, 3-octyne-1,2-diol, 3-octyne-1,5-diol, 3-octyne-1,6-diol, 3-octyne-1,7-diol, 3-octyne-1,8-diol, 3-octyne-2,5-diol, 3-octyne-2,6-diol, 3-octyne-2,7-diol, 3-octyne-2,8-diol, 3-octyne-5,6-diol, 3-octyne-5,7-diol, 3-octyne-5,8-diol, 3-octyne-6,7-diol, 3-octyne-6,8-diol, 3-octyne-7,8-diol, 4-octyne-1,2-diol, 4-octyne-1,3-diol, 4-octyne-1,6-diol, 4-octyne-1,7-diol, 4-octyne-1,8-diol, 4-octyne-2,3-diol, 4-octyne-2,6-diol, 4-octyne-2,7-diol, 4-octyne-2,8-diol, 4-octyne-3,6-diol, 4-octyne-3,7-diol, and 4-octyne-3,8-diol; and alkynyl amines in which a part of or all of the OH groups of the above alkynyl alcohols are substituted with $NH_2$ groups. The alkyne compounds and the alkene compounds are preferably used in an amount in the range of 0.1 to 100 equivalents, and more preferably in the range of 1 to 10 equivalents per mole of palladium.

As a palladium source that can be used in the reaction for producing the hydrogenation promoter, a palladium compound represented by any one of general formulae (1) to (4) or a multimer thereof is used. As the ligand L in these general formulae, either a monodentate ligand or a polydendate ligand can be used. Examples of the structure of ligand L include not only overall heteroatom-containing compounds other than phosphorus-containing compounds but also alkenes and alkynes. Examples thereof include amines such as ammonia, dimethylamine, trimethylamine, triethylamine, and N,N,N',N'-tetramethylethylenediamine; nitriles such as acetonitrile and benzonitrile; and amides such as N,N-dimethylformamide and N,N-dimethylacetamide. Examples of the anionic group X include fluorine, chlorine, bromine, iodine, sulfur, $NO_2$, $NO_3$, CN, OH, $SO_4$, $S_2O_3$, acetylacetone, a π-allyl group, a propionate group, a carboxyl group, and a $CF_3COO$ group.

Examples of the divalent palladium compound represented by general formula (1) include divalent neutral compounds that do not have a ligand L and divalent neutral compounds that have a ligand L. Among these, examples of divalent neutral compounds that do not have a ligand L include $PdF_2$, $PdCl_2$, $PdBr_2$, $PdI_2$, $Pd(OAc)_2$, $Pd(NO_3)_2$, $Pd(OH)_2$, $PdSO_4$, $Pd(CN)_2$, PdS, $Pd(OCOCF_3)_2$, bis(acetylacetone)palladium, and allylpalladium chloride. Examples of divalent neutral compounds that have a ligand L include $PdCl_2(NH_3)_2$, $PdBr_2(NH_3)_2$, $PdI_2(NH_3)_2$, $Pd(NO_2)_2(NH_3)_2$, $Pd(PhCN)_2Cl_2$, $Pd(CH_3CN)_2Cl_2$, (2,2-bipyridine)palladium dichloride, (1,5-cyclooctadiene)palladium dichloride, ethylenediamine palladium dichloride, N,N,N',N',-tetramethylethylenediamine palladium dichloride, and (1,10-phenanthroline)palladium dichloride. However, when a hydrogenation promoter derived from a divalent neutral compound that has a ligand L is used as a component of a hydrogenation catalyst, the rate of hydrogenation reaction may not be satisfactorily increased. Therefore, the divalent neutral compounds that do not have a ligand L are preferably used.

Examples of the divalent palladium compound represented by general formula (2) include divalent dianionic compounds such as $[PdCl_4]^{2-}(2NH_4)^{2+}$, $[Pd(S_2O_3)_4]^{2-}(2K)^{2+}$, $[PdCl_4]^{2-}(2K)^{2+}$, $[PdBr_4]^{2-}(2K)^{2+}$, $[PdCN_4]^{2-}(2K)^{2+}$, $[Pd(NO_2)_4]^{2-}(2K)^{2+}$, and $[PdCl_4]^{2-}(2Na)^{2+}$.

Examples of the divalent palladium compound represented by general formula (3) include divalent dicationic compounds such as $[Pd(NH_3)_4]^{2+}(2CH_3COO)^{2-}$, $[Pd(NH_3)_4]^{2+}(2Cl)^{2-}$, $[Pd(NH_3)_4]^{2+}(2Br)^{2-}$, $[Pd(NH_3)_4]^{2+}(2NO_3)^{2-}$, $[Pd(NH_3)_4]^{2+}(PdCl_4)^{2-}$, $[Pd(dmf)_4]^{2+}(2Cl)^{2-}$, $[Pd(dmf)_4]^{2+}(2BF_4)^{2-}$, $[Pd(dmf)_4]^{2+}(2ClO_4)^{2-}$, $[Pd(dmf)_4]^{2+}(2PF_6)^{2-}$, $[Pd(dmf)_4]^{2+}(2I_3)^{2-}$, $[Pd(dmf)_4]^{2+}(2I)^{2-}$, $[Pd(dmf)_4]^{2+}(2CF_3SO_3)^{2-}$, $[Pd(dma)_4]^{2+}(2Cl)^{2-}$, $[Pd(dma)_4]^{2+}(2BF_4)^{2-}$, $[Pd(dma)_4]^{2+}(2ClO_4)^{2-}$, $[Pd(dma)_4]^{2+}(2PF_6)^{2-}$, $[Pd(dma)_4]^{2+}(2I_3)^{2-}$, $[Pd(dma)_4]^{2+}(2I)^{2-}$, $[Pd(dma)_4]^{2+}(2CF_3SO_3)^{2-}$, $[Pd(CH_3CN)_4]^{2+}(2Cl)^{2-}$, $[Pd(CH_3CN)_4]^{2+}(2BF_4)^{2-}$, $[Pd(CH_3CN)_4]^{2+}(2ClO_4)^{2-}$, $[Pd(CH_3CN)_4]^{2+}(2PF_6)^{2-}$, $[Pd(CH_3CN)_4]^{2+}(2I_3)^{2-}$, $[Pd(CH_3CN)_4]^{2+}(2I)^{2-}$, $[Pd(CH_3CN)_4]^{2+}(2CF_3SO_3)^{2-}$, $[Pd(PhCN)_4]^{2+}(2Cl)^{2-}$, $[Pd(PhCN)_4]^{2+}(2BF_4)^{2-}$, $[Pd(PhCN)_4]^{2+}(2ClO_4)^{2-}$, $[Pd(PhCN)_4]^{2+}(2PF_6)^{2-}$, $[Pd(PhCN)_4]^{2+}(2I_3)^{2-}$, $[Pd(PhCN)_4]^{2+}(2I)^{2-}$, and $[Pd(PhCN)_4]^{2+}(2CF_3SO_3)^{2-}$. Regarding a process of producing such a divalent dicationic compound, for example, $[Pd(CH_3CN)_4]^{2+}(2BF_4)^{2-}$ can be obtained by reacting palladium sponge with $NOBF_4$ in acetonitrile solvent (Organometallics Vol. 20, p. 2697 (2001)). Furthermore, the ligand L of a palladium compound can be converted into a ligand having a higher coordination ability. For example, $[Pd(dmf)_4]^{2+}$ $(2BF_4)^{2-}$ can be synthesized from $[Pd(CH_3CN)_4]^{2+}(2BF_4)^{2-}$ (Inorg. Chem., Vol. 30, p. 1112 (1991)).

Examples of the tetravalent dianionic compounds represented by general formula (4) include $[PdCl_6]^{2-} (2NH_4)^{2+}$, $[PdCl_6]^{2-}(2K)^{2+}$, and $[PdCl_6]^{2-}(2Na)^{2+}$.

As regards the base that can be used in the reaction for producing the hydrogenation promoter, examples of the base include inorganic bases such as metal alkoxides, metal aryloxides, hydroxides, alkyl metal compounds, aryl metal compounds, and ammonia; and organic bases such as amines, imines, amides, and imides. Basic reducing agents may also be used. Mixtures thereof may also be used. Specific examples thereof include $CH_3OK$, $CH_3CH_2OK$, $CH_3CH_2CH_2OK$, i-PrOK, tert-BuOK, tert-AmOK, $(CH_3CH_2)_3COK$, PhOK, $CH_3ONa$, $CH_3CH_2ONa$, $CH_3CH_2CH_2ONa$, i-PrONa, tert-BuONa, tert-AmONa, $(CH_3CH_2)_3CONa$, PhONa, $CH_3OLi$, $CH_3CH_2OLi$, $CH_3CH_2CH_2OLi$, I-PrOLi, tert-BuOLi, tert-AmOLi, $(CH_3CH_2)_3COLi$, PhOLi, KOH, $K_2CO_3$, NaOH, LiOH, $Ca(OH)_2$, $Mg(OH)_2$, MeLi, n-BuLi, tert-BuLi, PhLi, $NH_3$, $Me_3N$, $Me_2NH$, $MeNH_2$, $Et_3N$, $Et_2NH$, $EtNH_2$, $(n-Pr)_3N$, $(n-Pr)_2NH$, $n-PrNH_2$, $(i-Pr)_2Nh$, $i-PrNH_2$, n-dibutylamine, n-butylamine, tert-butylamine, quinoline, pyridine, picoline, 1,8-diazabicyclo [5,4,0]undec-7-ene (DBU), and 1,4-diazabicyclo[2,2,2]octane (DABCO). Among these, alkoxides of an alkali metal and aryloxides of an alkali metal are preferred. Compounds containing potassium, which is highly basic, as the alkali metal are more preferred. For example, $CH_3OK$, tert-BuOK, tert-AmOK, $(CH_3CH_2)_3COK$, and PhOK are even more preferred. These bases may react with an organic solvent to produce a compound having a reducing property, and the compound may react with a palladium compound to produce palladium nanoparticles. Examples of the reducing agent include, but are not particularly limited to, borohydride compounds, borane compounds, metal hydrides, organolithium compounds, alcohols, aldehydes, formic acid compounds, hydrogen, and mixtures thereof. Specific examples thereof include $LiBH_4$, $NaBH_4$, $KBH_4$, $Me_4NBH_4$, $Bu_4NBH_4$, $Ca(BH_4)_2$, $LiEt_3BH$, diborane, LiH, NaH, KH, $LiAlH_4$, diisobutylaluminum hydride, Red-Al, methyllithium, butyllithium, hydrazine, methanol, ethanol, n-propyl alcohol, isopropyl alcohol, n-butyl alcohol, sec-butylalcohol, formaldehyde, formic acid, lithium formate, sodium formate, potassium formate, and ammonium formate. The amount of the base or reducing agent used is not particularly limited. Preferably, the number of equivalents of the base or reducing agent is roughly equal to the valence of the palladium compound used. For example, when a divalent palladium compound is used, the base or the reducing agent is used preferably in an amount in the range of 0.5 to 50 equivalents, more preferably in the range of 1 to 10 equivalents, and even more preferably in the range of 1.5 to 2.5 equivalents per mole of palladium. When these compounds are added in excessive amounts, agglomeration of resulting palladium nanoparticles may occur. In the reaction for preparing the hydrogenation promoter of the present invention, when an alkynyl alcohol compound is used as an alkyne compound, or an alkenyl alcohol compound is used as an alkene compound, the compound also functions as a reducing agent. Therefore, the hydrogenation promoter can be obtained without separately using a base or a reducing agent.

The reaction for producing the hydrogenation promoter is preferably conducted under an atmosphere of an inert gas such as argon or nitrogen gas that does not contain oxygen. The reaction temperature is not particularly limited, but is preferably in the range of 10° C. to 100° C. and more preferably in the range of 10 ° C. to 40° C. The reaction time is also not particularly limited, but is preferably in the range of 1 to 72 hours and more preferably in the range of 3 to 10 hours. This production reaction is conducted, for example, as follows. An organic solvent is added to a reactor under an inert gas atmosphere, an alkyne compound or an alkene compound is added thereto, at least one palladium compound selected from the group consisting of palladium compounds represented by general formulae (1) to (4) or at least one multimer thereof is then added under stirring, a base is gradually added, and the mixture is further stirred. As the reaction proceeds, the color tone of the reaction solution gradually changes to a dark brown. The generation of the hydrogenation promoter can be confirmed by this change in color.

The hydrogenation catalyst of the present invention includes the above-described hydrogenation promoter itself; a catalyst including at least one palladium compound selected from the group consisting of palladium compounds represented by general formulae (1) to (4) or at least one multimer thereof, and a base and/or a reducing agent; a catalyst including the above-described hydrogenation promoter, and a base and/or a reducing agent; and a catalyst including palladium nanoparticles and a borohydride compound. When the above-described hydrogenation promoter is used alone as the hydrogenation catalyst, a hydrogenation reaction from an alkyne compound to an alkene compound can be conducted at a very high rate using a trace amount thereof. However, when an internal alkyne compound is used as a reaction substrate, it may be difficult to produce a cis-alkene compound with high selectivity. When the catalyst including at least one palladium compound selected from the group consisting of palladium compounds represented by general formulae (1) to (4) or at least one multimer thereof, and a base and/or a reducing agent is used as the hydrogenation catalyst, a hydrogenation reaction from an alkyne compound to an alkene compound can be conducted at a relatively high rate. In addition, when an internal alkyne compound is used as a reaction substrate, a hydrogenation reaction that produces a cis-alkene compound is conducted with high selectivity. In this case, it is believed that palladium nanoparticles are produced in the reaction system, and these palladium nanoparticles function as a hydrogenation promoter, thus the hydrogenation reaction is conducted. When the catalyst including the above-described hydrogenation promoter, and a base and/or a reducing agent; or the catalyst including palladium nanoparticles and a borohydride compound is used as a hydrogenation catalyst, a hydrogenation reaction from an alkyne compound to an alkene compound can be conducted at a very high rate using a trace amount thereof. In addition, when an internal alkyne compound is used as a reaction substrate, a hydrogenation reaction that produces a cis - alkene compound is conducted with high selectivity. Palladium nanoparticles prepared by a known process may also be used. However, the use of the hydrogenation promoter of the present invention, i.e., the palladium nanoparticles containing an alkyne compound or an alkene compound as an agglomeration-preventing agent can provide a hydrogenation catalyst having a higher performance.

The hydrogenation catalyst including the above-described hydrogenation promoter, and a base and/or a reducing agent can be prepared by mixing the hydrogenation promoter with the base and/or the reducing agent. This mixing operation may be performed by directly charging the base and/or the reducing agent into the hydrogenation promoter (reaction solution) or by charging the hydrogenation promoter and the base and/or the reducing agent into a solvent that can dissolve these compounds. Before hydrogenation reaction, the hydrogenation promoter and the base and/or the reducing agent may be mixed in advance to prepare the hydrogenation catalyst. Alternatively, during hydrogenation reaction, the hydrogenation promoter, and the base and/or the reducing agent may be charged into the reaction system and mixed to prepare the hydrogenation catalyst. The role of the base and the reducing agent here is that mainly when a partial hydrogenation reaction of an internal alkyne compound is conducted, a phenomenon in which a cis-alkene, which once produced, is isomerized or excessively hydrogenated by being subjected to an interaction with the palladium catalyst again is suppressed. A reducing agent often has a marked effect of suppressing these side reactions compared with a base. When a reducing agent is used, a cis-alkene having a high purity tends to be obtained. Accordingly, when the structure of an alkyne compound (substrate) to be partially hydrogenated does not include such a substituent that directly reacts with a reducing agent, the reduction agent is preferably added. When a substrate includes a substituent such as a carbonyl group, the addition of a reducing agent is not preferable because the substrate directly reacts with the reducing agent. In such a case, a base is preferably added. Furthermore, plural types of bases or reducing agents may be used, or bases and reducing agents may be used in combinations. Although the term "hydrogenation catalyst" is used here, it is not known at present whether a hydrogenation promoter reacts with a base and/or a reducing agent to produce an active species different from the hydrogenation promoter or whether a hydrogenation promoter does not react with a base and/or a reducing agent and acts alone. In either case, since it has been demonstrated that the problems of the present invention can be solved, the term "hydrogenation catalyst" is used for convenience.

As regards the base that can be used in the reaction for producing the hydrogenation catalyst, examples of the base include inorganic bases such as metal alkoxides, metal aryloxides, hydroxides, alkyl metal compounds, aryl metal compounds, and ammonia; and organic bases such as amines, imines, amides, and imides. Mixtures thereof may also be used. Specific examples thereof include $CH_3OK$, $CH_3CH_2OK$, $CH_3CH_2CH_2OK$, i-PrOK, tert-BuOK, tert-AmOK, $(CH_3CH_2)_3COK$, PhOK, $CH_3ONa$, $CH_3CH_2ONa$, $CH_3CH_2CH_2ONa$, i-PrONa, tert-BuONa, tert-AmONa, $(CH_3CH_2)_3CONa$, PhONa, $CH_3OLi$, $CH_3CH_2OLi$, $CH_3CH_2CH_2OLi$, i-PrOLi, tert-BuOLi, tert-AmOLi, $(CH_3CH_2)_3COLi$, PhOLi, KOH, NaOH, LiOH, $Ca(OH)_2$, $Mg(OH)_2$, $K_2CO_3$, MeLi, n-BuLi, tert-BuLi, PhLi, $NH_3$, $Me_3N$, $Me_2NH$, $MeNH_2$, $Et_3N$, $Et_2NH$, $EtNH_2$, $(n-Pr)_3N$, $(n-Pr)_2NH$, $n-PrNH_2$, $(i-Pr)_2NH$, $i-PrNH_2$, n-dibutylamine, n-butylamine, tert-butylamine, quinoline, pyridine, picoline, DBU, and DABCO. Among these, alkoxides of an alkali metal and aryloxides of an alkali metal are preferred. Bases containing lithium or sodium as the alkali metal are more preferred, and $CH_3ONa$, tert-BuONa, tert-AmONa, $(CH_3CH_2)_3CONa$, PhONa, $CH_3OLi$, tert-BuOLi, tert-AmOLi, $(CH_3CH_2)_3COLi$, and PhOLi are even more preferred. Since the amount of the base used differs depending on impurities contained in the substrate in addition to the type of substrate and type of base used, an appropriate amount may be determined case by case. The amount of the base used is preferably in the range of 0.00001 to 10 equivalents relative to the substrate, and 1 equivalent or more relative to the catalyst. Acidic components, ketones, peroxides, or the like may be contained in the substrate as impurities. When these impurities are removed by purifying the substrate, the amount of the base added can be reduced.

Examples of the reducing agent that can be used in the reaction for producing the hydrogenation catalyst include borohydride compounds, borane compounds, and metal hydrides. Specific examples thereof include $LiBH_4$, $NaBH_4$, $KBH_4$, $Me_4NBH_4$, $Bu_4NBH_4$, $Ca(BH_4)_2$, $LiEt_3BH$, diborane, a dimethylamine-borane complex, a pyridine-borane complex, LiH, NaH, KH, $LiAlH_4$, diisobutylaluminum hydride, and Red-Al. Among these, borohydride compounds are preferred, and $LiBH_4$, $NaBH_4$, $KBH_4$, $BU_4NBH_4$, and $Me_4NBH_4$ are particularly preferred. Since the amount of the reducing agent used differs depending on impurities contained in the substrate in addition to the type of substrate and type of reducing agent used, an appropriate amount may be determined case by case. The amount of the reducing agent used is preferably in the range of 0.000001 to 0.01 equivalents relative to the substrate, and 1 equivalent or more relative to the catalyst. Acidic components, ketones, peroxides, or the like may be contained in the substrate as impurities. When these impurities are removed by purifying the substrate, the amount of the reducing agent added can be reduced.

According to a process for producing an alkene compound of the present invention, the alkene compound is produced by partially hydrogenating an alkyne compound, which is a reaction substrate, using the above-described hydrogenation catalyst in a reaction solvent in the presence of hydrogen or a compound that provides hydrogen. In cases where a catalyst including at least one palladium compound selected from the group consisting of palladium compounds represented by general formulae (1) to (4) or at least one multimer thereof, and a base and/or a reducing agent; or a catalyst including the above-described hydrogenation promoter, and a base and/or a reducing agent is used as the hydrogenation catalyst, when the alkyne compound is an internal alkyne compound, a cis-alkene compound is highly selectively produced.

Furthermore, when the hydrogenation catalyst is treated with hydrogen gas in advance and hydrogenation reaction of an alkyne compound is then conducted, the hydrogenation reaction may proceed at a higher rate. It is believed that the agglomeration-preventing agent covering palladium nanoparticles is hydrogenated by this preliminary treatment, and thus the nanoparticles are slightly agglomerated to increase the particle diameter. In particular, when a hydrogenation reaction of a terminal alkyne compound is conducted, this preliminary treatment is effective in some cases. The time required for the preliminary treatment with hydrogen gas is not particularly limited, but may be determined to be, for example, in the range of 10 to 60 minutes.

The amount of hydrogenation catalyst used in the process for producing an alkene compound of the present invention differs depending on the reactor used and economical efficiency. However, the hydrogenation catalyst can be used so that the S/C (amount of substrate/amount of catalyst) ratio for the alkyne compound, which is a reaction substrate, is in the range of 10 to 100,000,000 and preferably in the range of 500 to 5,000,000. For the purpose of this description, when the S/C ratio is calculated, "C" is defined as the amount of palladium contained in the catalyst.

As the reaction solvent used in the process for producing an alkene compound of the present invention, appropriate solvents such as protic solvents, aprotic solvents, coordinating solvents, and mixed solvents thereof can be used. Examples of protic solvents include alcohol solvents such as methanol, ethanol, 1-propanol, 2-propanol, 1-butanol, tert-butyl alcohol, and benzyl alcohol; water; and mixed solvents thereof. Examples of aprotic solvents include aromatic hydrocarbon solvents such as toluene and xylenes; aliphatic hydrocarbon solvents such as pentane, n-hexane, and cyclohexane; halogen-containing hydrocarbon solvents such as methylene chloride, chloroform, and dichloroethane; ether solvents such as diethyl ether, diisopropyl ether, methyl-tert-butyl ether, and THF; and mixed solvents thereof. Examples of coordinating solvents include heteroatom-containing organic solvents such as acetonitrile, DMA, DMF, N-methylpyrrolidone, and DMSO; and mixed solvents thereof. Among these, ether solvents, DMF, DMA, and alcohol solvents are preferred, and THF, DMF, and DMA are even more preferred.

When hydrogen is used in the process for producing an alkene compound of the present invention, it is sufficient that the hydrogen pressure is 1 atm or less because the catalyst system used in this process is extremely highly active. However, in view of economical efficiency and safety, the hydrogen pressure is preferably in the range of 1 to 50 atm and more preferably in the range of 3 to 10 atm.

The reaction temperature in the process for producing an alkene compound of the present invention is not particularly limited, but may be, for example, in the range of −15° C. to 100° C., and preferably in the range of 20° C. to 40° C. The reaction time differs depending on the reaction conditions such as the type of hydrogenation catalyst used, the S/C ratio, the type of reaction substrate, the concentration, the solvent, the temperature, and the pressure. However, in order to conduct the reaction easily, the S/C ratio and the like are preferably set so that the reaction time is in the range of 1 minute to 1 hour.

The alkyne compound to which the process for producing an alkene compound of the present invention can be applied is not particularly limited. Examples thereof include compounds that have been cited as examples of alkyne compounds that can be used in the reaction for producing the hydrogenation promoter.

Acidic components, ketones, peroxides, metals, ions, or the like may be contained in the alkyne compound as impurities. Since these impurities cause an inhibition of hydrogenation reaction or a decrease in the cis-selectivity, preferably, the alkyne compound is purified to remove the impurities and is then provided to the hydrogenation reaction. A large amount of an inorganic salt may also inhibit hydrogenation reaction. In order to remove acidic components from the alkyne compound, a method of washing with an alkaline compound is effective. Examples of the alkaline compound include alkali metal compounds such as sodium hydroxide, potassium hydroxide, sodium hydrogencarbonate, sodium carbonate, and potassium carbonate; aqueous solutions thereof; aqueous ammonia; an aqueous solution of dimethylamine; and an aqueous solution of diethylamine. If the alkyne compound is a solid at room temperature, the alkyne compound is preferably diluted with a solvent and then washed with an alkaline aqueous solution. In such a case, acidic components can be efficiently removed. If the alkyne compound is a liquid at room temperature, the solvent is not necessarily used. If the alkyne compound is miscible with water, the alkaline compound is preferably used without further treatment, i.e., not in an aqueous solution. It is more effective that, after the alkali treatment of the alkyne compound, the alkaline component is removed by washing with water, and purification such as recrystallization or distillation is then performed. In order to remove ketones and peroxides from the alkyne compound, a treatment method using a reducing agent to allow the ketones and the peroxides to be harmless is effective. Specific examples of the reducing agent include $LiBH_4$, $NaBH_4$, $KBH_4$, $Me_4NBH_4$, $Bu_4NBH_4$, $Ca(BH_4)_2$, $LiEt_3BH$, $LiH$, $NaH$, $KH$, $LiAlH_4$, diisobutylaluminum hydride, and Red-Al. If the alkyne compound is a solid at room temperature, preferably, the alkyne compound is diluted with a solvent that is nonreactive to the reducing agent, the reducing agent is then added, and the mixture is stirred. In such a case, ketones and the like can be efficiently changed to be harmless. If the alkyne compound is a liquid at room temperature, the solvent need not be used. It is more effective that, after the alkyne compound is treated with a reducing agent, the reducing agent is removed by washing with water, and purification such as recrystallization or distillation is then performed. When the alkyne compound is provided to a hydrogenation reaction without performing purification, i.e., in a state in which impurities such as acids or ketones are present, the amount of base and/or reducing agent constituting the hydrogenation catalyst is increased, thereby allowing the hydrogenation reaction to be conducted with high selectivity. Since the amount of base and/or reducing agent to be increased differs depending on the type and the amount of impurities, the amount of base and/or reducing agent must be determined with appropriate consideration. Furthermore, when trace amounts of acidic components, ketones, peroxides, or the like are present in the solvent used in the hydrogenation reaction, preferably, purification is performed or the amount of base or reducing agent added is appropriately increased.

In the process for producing an alkene compound of the present invention, an additive may be further added in the reaction system. Examples of the additive include nitrogen-containing compounds such as $NH_3$, $Me_3N$, $Me_2NH$, $MeNH_2$, $Et_3N$, $Et_2NH$, $EtNH_2$, $(n-Pr)_3N$, $(n-Pr)_2NH$, $n-PrNH_2$, $(i-Pr)_2NH$, $i-PrNH_2$, n-dibutylamine, n-butylamine, tert-butylamine, quinoline, pyridine, picoline, aniline, DBU, DABCO, N,N,N',N'-tetramethylethylenediamine (TMEDA), N,N'-dimethylethylenediamine, acetonitrile, benzonitrile, and N,N-dimethylaminoethanol; alcohols such as ethylene glycol, trifluoroethanol, phenol, and p-nitrophenol; phosphorus-containing compounds such as triphenylphosphine, diphenylphosphino methane, diphenylphosphino ethane, and triphenylphosphine oxide; host compounds such as 12-crown-4, 15-crown-5, 18-crown-6, and cryptands; and water. In some reaction systems, by adding these additives, isomerization from a cis-alkene compound to a trans-alkene compound is suppressed, or over-reduction from an alkene compound to an alkane compound is suppressed, thereby obtaining an alkene compound having a high purity.

Since the hydrogenation catalyst of the present invention conducts hydrogenation of an alkyne at a very high rate, it is difficult to trap the true active species. However, it is believed that when at least one palladium compound selected from the group consisting of palladium compounds represented by general formulae (1) to (4) or at least one multimer thereof, and a base and/or a reducing agent are combined to be used as the hydrogenation catalyst, the same active species is provided in all cases. Since the active species has an excellent property in terms of performance, all the problems to be solved by the present invention can be solved.

EXAMPLES

Next, the present invention will be described more specifically using examples, but the present invention is not limited to these examples. The reaction in each example described below was conducted under an atmosphere of an inert gas such as argon gas or nitrogen gas. A dried and deaerated solvent was used in the reaction. A substrate that was washed with a 1% aqueous solution of sodium carbonate to remove an acidic component, and then purified by distillation was used unless otherwise stated. The conversion rate from an alkyne compound to an alkene compound and the selectivity from an internal alkyne compound to a cis-alkene compound were measured by gas chromatography (GC). A GC-17A (manufactured by Shimadzu Corporation) was used as the GC system. A capillary column CP-Sil PONA CB (manufactured by VARIAN, Inc.) having an inner diameter of 0.25 mm and a length of 100 m was used as the column, and the measurement was performed at a temperature of 65° C. (fixed temperature). A RINT2100Ultima+/PC (manufactured by Rigaku Corporation) was used as an X-ray diffractometer.

Example 1

A novel hydrogenation promoter, prepared by reacting $PdCl_2$, 4-octyne serving as an alkyne, and KOtBu serving as a base in DMF, was synthesized as follows. Specifically, $PdCl_2$ (32.4 mg, 0.183 mmol) serving as a palladium compound was charged into a 20-mL Schlenk reaction tube equipped with a stirrer. Subsequently, DMF (18.3 mL) and 4-octyne (0.268 mL, 1.83 mmol) were added to the reaction tube under an argon atmosphere, and the mixture was stirred. Subsequently, when KOtBu (41.0 mg, 0.366 mmol, 2.0 equivalents relative to Pd) was added and the mixture was stirred, a reaction was initiated, the color tone of the solution changed to a dark brown, and $PdCl_2$, which had been insoluble in DMF, gradually dissolved and disappeared. It is believed that this shows the hydrogenation promoter is produced. The reaction solution was then stirred at room temperature for three hours to yield a DMF solution containing a target hydrogenation promoter (1).

An X-ray diffraction measurement of the prepared hydrogenation promoter (1) was performed. A diffraction corresponding to Pd(111) was observed at 2θ=39.4 (deg), and a diffraction corresponding to Pd(220) was observed at 70 (deg). Thus, the hydrogenation promoter was identified to be the zero-valent palladium. The average crystal diameter was calculated from the half-width of a diffraction peak to be 1.6 nm. Consequently, the hydrogenation promoter of Example 1 was identified as being composed of palladium nanoparticles having an average crystal diameter of 1.6 nm. Table 1 shows the result of Example 1.

Examples 2 to 27 and A to G

Table 1 also shows the results of Examples 2 to 17 and A to G. Examples 2 to 17 and A to G are synthetic examples of hydrogenation promoters prepared using various types of palladium compound, various types of base or reducing agent, and various types of alkyne compound. The synthesis was performed under the same reaction conditions as in Example 1. However, in Example 5, the base was used in an amount of 8 equivalents relative to Pd. In this description, the prepared hydrogenation promoters are referred to as hydrogenation promoters (2) to (17) and (A) to (G).

TABLE 1

| Example[X.1] | Pd compound | Base or Reducing agent | alkyne | Hydrogenation promoter | Crystal diameter (nm)[X.2] |
|---|---|---|---|---|---|
| 1 | $PdCl_2$ | KOtBu | 4-octyne | Hydrogenation promoter 1 | 1.6 |
| 2 | $Na_2PdCl_4$ | KOtBu | 4-octyne | Hydrogenation promoter 2 | — |
| 3 | $Pd(PhCN)_2Cl_2$ | KOtBu | 4-octyne | Hydrogenation promoter 3 | — |
| 4 | $Pd(OAc)_2$ | KOtBu | 4-octyne | Hydrogenation promoter 4 | 1.6 |
| 5 | $Pd(OAc)_2$ | KOtAm, 8 eq | 4-octyne | Hydrogenation promoter 5 | — |
| 6 | $PdBr_2$ | KOtBu | 4-octyne | Hydrogenation promoter(6) | — |
| 7 | $PdCl_2$ | KOtBu | 3-hexyne | Hydrogenation promoter 7 | — |
| 8 | $PdCl_2$ | KOtBu | diphenylacetylene | Hydrogenation promoter 8 | — |
| 9 | $PdCl_2$ | KOtBu | 2-butyne-1,4-diol | Hydrogenation promoter 9 | — |
| 10 | $PdCl_2$ | KOtBu | 3-hexyne-3,5-diol | Hydrogenation promoter 10 | — |
| 11 | $PdCl_2$ | KOtBu | 3-hexyne-1-ol | Hydrogenation promoter 11 | — |
| 12 | $Pd(OAc)_2$ | NaOtBu | 4-octyne | Hydrogenation promoter 12 | — |
| 13 | $PdCl_2$ | LiOtBu | 4-octyne | Hydrogenation promoter 13 | — |
| 14 | $Pd(OAc)_2$ | KOMe | 4-octyne | Hydrogenation promoter 14 | — |
| 15 | $PdCl_2$ | NaOMe | 4-octyne | Hydrogenation promoter 15 | — |
| 16 | $PdCl_2$ | NaOPh | 4-octyne | Hydrogenation promoter 16 | — |
| 17 | $Pd(OAc)_2$ | KOtBu | 2-butyne-1,4-diol | Hydrogenation promoter 17 | — |
| A | $PdCl_2$ | KOtBu | di(tert-butyl) acetylene | Hydrogenation promoter A | 1.8 |
| B | $Pd(OAc)_2$ | $NaBH_4$ | di(tert-butyl) acetylene | Hydrogenation promoter B | — |
| C | $Pd(OAc)_2$ | $Bu_4NBH_4$ | di(tert-butyl) acetylene | Hydrogenation promoter C | — |
| D | $Pd(OAc)_2$ | HCOOH | 4-octyne | Hydrogenation promoter(D) | 1.6 |
| E | $Pd(OAc)_2$ | $HCOONH_4$ | 4-octyne | Hydrogenation promoter(E) | 3.8 |
| F | $Pd(OAc)_2$ | $NaBH_4$ | 4-octyne | Hydrogenation promoter(F) | 1.6 |
| G | $Pd(OAc)_2$ | $Bu_4NBH_4$, | 4-octyne | Hydrogenation promoter(G) | 4.2 |

[X.1] In Examples 1-17 and A to G, DMF was used as a reaction solvent.
[X.2] The crystal diameter was calculated from the half-diffraction peak obtained by X-ray diffractometry.

Example 18

A novel hydrogenation promoter, prepared by reacting $Pd(OAc)_2$ with 2-butyne-1,4-diol in DMF without using a base or a reducing agent, was synthesized as follows. Specifically, $Pd(OAc)_2$ (42.0 mg, 0.187 mmol) serving as a palladium compound and 2-butyne-1,4-diol (0.161 g, 1.87 mmol) serving as an alkyne were charged to a 20-mL Schlenk reaction tube equipped with a stirrer. Subsequently, DMF (18.7 mL) was added under an argon atmosphere, and the mixture was stirred. A reaction was initiated, and the color tone of the solution changed to a dark brown. The reaction solution was stirred at room temperature for three hours to yield a DMF solution containing a target hydrogenation promoter (18). Table 2 shows the result of Example 18.

Examples H to K

Table 2 also shows the results of Examples H to K. Examples H to K are synthetic examples of hydrogenation promoters prepared using various types of alkynyl alcohol. The reaction was conducted as in Example 18. In this description, the prepared hydrogenation promoters are referred to as hydrogenation promoters (H) to (K).

TABLE 2

| Example[X.1] | Pd compound | Base or Reducing agent | alkyne | Hydrogenation promoter | Crystal diameter (nm)[X.2] |
|---|---|---|---|---|---|
| 18 | Pd(OAc)$_2$ | — | 2-butyne-diol | Hydrogenation promoter (18) | 1.6 |
| H | Pd(OAc)$_2$ | — | 3-hexyne-diol | Hydrogenation promoter(H) | 2.6 |
| I | Pd(OAc)$_2$ | — | 2-hexyne-ol | Hydrogenation promoter(I) | 1.4 |
| J | Pd(OAc)$_2$ | — | 5-hexyne-ol | Hydrogenation promoter(J) | 1.1 |
| K | Pd(OAc)$_2$ | — | 2-propylene-ol | Hydrogenation promoter(K) | 1.2 |

[X.1] In Examples 18 and H to K, DMF was used as a reaction solvent.
[X.2] A crystal diameter was calculated from the half-width of a diffraction peak obtained by X-ray diffratometry.

Example 19

A hydrogenation catalyst, containing a hydrogenation promoter and a reducing agent, was prepared as follows. Specifically, KBH$_4$ (80.9 mg, 1.5 mmol) was added to a 20-mL Schlenk reaction tube equipped with a stirrer, and 3 mL (Pd content=30 μmol) of a DMF solution (Pd concentration=10 μmol/mL) containing the hydrogenation promoter (1) prepared in Example 1, and 18 mL of DMF were added under an argon atmosphere. The mixture was stirred, thus yielding a target hydrogenation catalyst (1). Table 3 shows the result of Example 19.

Examples 20 to 23 and L

Table 3 also shows the results of Examples 20 to 23 and L. Examples 20 to 23 and L are synthetic examples of hydrogenation catalysts prepared using various types of hydrogenation promoter. In this description, the prepared hydrogenation catalysts are referred to as hydrogenation catalysts (2) to (5) and (L). The experiments of Examples 20 to 23 and L were conducted in accordance with the experimental procedure of Example 19.

TABLE 3

| Example | Hydrogenation promoter | Base or Reducing agent[X.1] | Hydrogenation catalyst |
|---|---|---|---|
| 19 | Hydrogenation promoter(1) | KBH$_4$, 50 eq | Hydrogenation catalyst(1) |
| 20 | Hydrogenation promoter(4) | KBH$_4$, 50 eq | Hydrogenation catalyst(2) |
| 21 | Hydrogenation promoter(5) | KBH$_4$, 50 eq | Hydrogenation catalyst(3) |
| 22 | Hydrogenation promoter(12) | KBH$_4$, 50 eq | Hydrogenation catalyst(4) |
| 23 | Hydrogenation promoter(14) | KBH$_4$, 50 eq | Hydrogenation catalyst(5) |
| L | Hydrogenation promoter(C) | Bu$_4$NBH$_4$, 20 eq | Hydrogenation catalyst(L) |

[X.1] eq is an equivalent amount relative to Pd

Example 24

An example of an alkene compound produced by partially hydrogenating an alkyne compound in the presence of a hydrogenation catalyst containing a hydrogenation promoter and a reducing agent will be described. First, 37.8 mg (1.00 mmol) of NaBH$_4$ was charged to a 100-mL glass autoclave which was equipped with a stirrer and whose periphery was kept at 30° C., and the autoclave was purged with argon gas. Subsequently, 10 mL of DMF, 1.47 mL (10 mmol) of 4-octyne, and 1.00 mL (Pd content=10 μmol) of the hydrogenation promoter (1) prepared in Example 1 were added to the autoclave under an argon atmosphere. A hydrogenation catalyst (1) composed of the hydrogenation promoter (1) and NaBH$_4$ was prepared in the autoclave by this operation. The autoclave was connected to a hydrogen gas cylinder via a gas-introducing tube, and air in the introducing tube was purged with hydrogen at 2 atm three times. Subsequently, hydrogen at 8 atm was introduced into the autoclave, and the hydrogen was then discharged carefully until the pressure was decreased to 2 atm. This operation was repeated seven times. The hydrogen pressure was then increased to 8 atm, and the solution was vigorously stirred at 30° C. Thereby, hydrogenation reaction proceeded. The conversion rate and the selectivity of cis-4-octene in the product were determined by GC. A trans isomer (trans-4-octene), positional isomers (trans-3-octene, cis-2-octene, and the like), and an excessively hydrogenated product (octane) were produced as by-products. Table 4 shows the result of this example. The selectivity described in Table 4 represents the ratio of the amount of cis isomer to the sum of all the amounts of alkenes (a cis isomer, a trans isomer, and positional isomers) and an alkane produced. This definition is also used for Table 5 and thereafter.

Examples 25 to 42

Table 4 also shows the results of Examples 25 to 42. Examples 25 to 42 are reaction examples in which hydrogenation catalysts were prepared in a reaction system during hydrogenation reaction using various types of hydrogenation promoter to conduct hydrogenation of 4-octyne. The experiments of these examples were conducted in accordance with the experimental procedure of Example 24.

TABLE 4

| Example | Hydrogenation promoter | Base or Reducing agent[×1] | S/C | Solvent | Reaction time (min) | Conversion rate (%) | Selectivity (%) |
|---|---|---|---|---|---|---|---|
| 24 | Hydrogenation promoter(1) | NaBH$_4$, 100 eq | 1000 | DMF | 4 | 100 | 99.7 |
| 25 | Hydrogenation promoter(1) | — | 1000 | DMF | 5 | 100 | 26.9 |
| 26 | Hydrogenation promoter(1) | NaBH$_4$, 50 eq | 20000 | DMF | 5 | 100 | 98.1 |
| 27 | Hydrogenation promoter(1) | KBH$_4$, 50 eq | 20000 | DMF | 5 | 99.9 | 98.7 |
| 28 | Hydrogenation promoter(1) | KOtBu, 50 eq | 20000 | DMF | 5 | 100 | 96.4 |
| 29 | Hydrogenation promoter(1) | — | 20000 | DMF | 10 | 100 | 56.2 |
| 30 | Hydrogenation promoter(2) | NaOtBu, 200 eq | 1000 | DMF + tBuOH[×2] | 2.5 | 100 | 98.8 |
| 31 | Hydrogenation promoter(3) | KBH$_4$, 50 eq | 20000 | DMF | 10 | 99.9 | 98.7 |
| 32 | Hydrogenation promoter(4) | NaBH$_4$, 100 eq | 1000 | DMF | 5 | 100 | 99.6 |
| 33 | Hydrogenation promoter(5) | KBH$_4$, 50 eq | 20000 | DMF | 5 | 100 | 98.5 |
| 34 | Hydrogenation promoter(6) | NaOtBu, 200 eq | 1000 | DMF + tBuOH[×2] | 2 | 100 | 97.2 |
| 35 | Hydrogenation promoter(7) | NaBH$_4$, 100 eq | 1000 | DMF | 3 | 100 | 99.6 |
| 36 | Hydrogenation promoter(8) | NaBH$_4$, 100 eq | 1000 | DMF | 4 | 100 | 99.2 |
| 37 | Hydrogenation promoter(9) | NaBH$_4$, 100 eq | 1000 | DMF | 6 | 100 | 99.9 |
| 38 | Hydrogenation promoter(10) | NaBH$_4$, 100 eq | 1000 | DMF | 4 | 100 | 98.8 |
| 39 | Hydrogenation promoter(11) | NaBH$_4$, 100 eq | 1000 | DMF | 3.5 | 100 | 99.5 |
| 40 | Hydrogenation promoter(12) | NaBH$_4$, 100 eq | 1000 | DMF + tBuOH[×2] | 4 | 100 | 99.5 |
| 41 | Hydrogenation promoter(15) | NaBH$_4$, 100 eq | 1000 | DMF + tBuOH[×2] | 120 | 96.8 | 99.8 |
| 42 | Hydrogenation promoter(16) | NaBH$_4$, 100 eq | 1000 | DMF + tBuOH[×2] | 7 | 100 | 99.6 |

[×1] eq is an equivalent amount relative to Pd
[×2] A mixed solvent of DMF:tBuOH = 19:1 was used as DMF + tBuOH Both Examples 24 and 25 are reaction examples in which S/C=1,000. The selectivity in Example 24 in which a reducing agent was added was markedly increased compared with that in Example 25 in which no reducing agent was added. These results showed that the reducing agent played an important role. All Examples 26 to 29 are reaction examples in which S/C=20,000. The reaction time in Example 26 in which S/C=20,000 was not significantly different from that in Example 24 in which S/C=1,000. The comparison of Example 26 in which NaBH$_4$ was used as the reducing agent with Example 27 in which KBH$_4$ was used as the reducing agent suggested that various types of compound could be used as the borohydride compound. The result of Example 28 in which a base was used instead of a reducing agent suggested that the base had an effect of increasing the selectivity, the effect being somewhat weaker than that of the reducing agent. The result of Example 29, in which neither a base nor a reducing agent was used, suggested that a satisfactory selectivity could not be achieved though hydrogenation reaction was conducted at a high rate in the presence of only the hydrogenation promoter. The result of Example 30 in which the hydrogenation promoter (2), prepared by using Na$_2$PdCl$_4$ as a palladium source, was used, suggested that when a hydrogenation catalyst, containing a base and a hydrogenation promoter prepared by using a divalent dianionic palladium compound, was used, the hydrogenation catalyst also had a satisfactory performance. The result of Example 31 in which the hydrogenation promoter (3), prepared by using Pd(PhCN)$_2$Cl$_2$ as a palladium source, was used, suggested that when a hydrogenation catalyst, containing a reducing agent and a hydrogenation promoter prepared by using a divalent neutral palladium compound having a ligand, was used, the hydrogenation catalyst also had a satisfactory performance. The results of Examples 32 and 34 in which the hydrogenation promoters (4) and (6), prepared by using Pd(OAc)$_2$ and PdBr$_2$ as a palladium source, respectively, were used, suggested that, for example, various types of divalent neutral palladium compound other than PdCl$_2$ could be used as the palladium source for preparing the hydrogenation promoter. The comparison of Example 33 in which the hydrogenation promoter (5) prepared by using KOtAm as a base was used with Example 32 in which the hydrogenation promoter (4), prepared by using KOtBu as a base, was used, suggested that various types of metal alkoxide could be used for preparing a hydrogenation promoter. The results of Examples 35 to 39 in which the hydrogenation promoters (7) to (11), prepared by using various types of alkyne compound, were used, respectively, suggested that internal alkynes other than 4-octyne could also be used equivalently as the alkyne compound used in the preparation of the hydrogenation promoter. The results of Examples 40 to 42 in which the hydrogenation promoters (12), (15), and (16), prepared by using various types of sodium alkoxide as a base, were used, respectively, showed that the use of sodium tert-butoxide or sodium phenoxide as the metal alkoxide for preparing the hydrogenation promoter provided a more satisfactory performance than the case where sodium methoxide was used.

Examples 43 to 47 ad M to X

Table 5 shows the results of Examples 43 to 47 and M to X. These examples are hydrogenation reaction examples of 4-octyne. Except for Example N, these examples are hydrogenation reaction examples in which a hydrogenation promoter prepared by using Pd(OAc)$_2$ as a palladium source, was used. Among these, Examples 44, 45, M, and U to X are hydrogenation reaction examples in which a hydrogenation promoter, prepared by adding an alkynyl alcohol without using a base, was used. Example 46 is a hydrogenation reaction example in which Pd(OAc)$_2$ was used without further treatment. Example 47 is a hydrogenation reaction example in which the hydrogenation promoter (17), prepared by adding a base and an alkynyl alcohol, was used. The hydrogenation reaction in these examples was performed in accordance with Example 24.

same performance. The comparison of Example 44 with Example 45 showed that the use of a hydrogenation catalyst containing a hydrogenation promoter and a reducing agent provided a higher selectivity than the case where the hydrogenation promoter was used as a hydrogenation catalyst without further treatment. The comparison of Example 46 with Examples 43, 44, and 47 showed that the use of a hydrogenation catalyst containing a hydrogenation promoter and a reducing agent increased the rate of hydrogenation reaction compared with the case where a hydrogenation catalyst containing a divalent neutral palladium compound and the reducing agent was used. The results of Examples Q to T showed that various types of compound could be used as a reducing agent for preparing a hydrogenation promoter. The results of Examples 44, 45, M, and U to X showed that various types of compound could be used as an alkynyl alcohol for preparing a hydrogenation promoter.

Examples 48 to 53 and AA

Table 6 shows the results of Examples 26, 28, P, 48 to 53, and AA. Examples 48 to 53 and AA are reaction examples in

TABLE 5

| Example | Hydrogenation promoter and the like | Base or Reducing agent[X1] | S/C | Solvent | Reaction time (min) | Conversion rate (%) | Selectivity (%) |
|---|---|---|---|---|---|---|---|
| 43 | Hydrogenation promoter(4) | KBH$_4$, 50 eq | 20000 | DMF | 10 | 99.8 | 99.3 |
| 44 | Hydrogenation promoter(18) | KBH$_4$, 50 eq | 20000 | DMF | 10 | 100 | 99.3 |
| 45 | Hydrogenation promoter(18) | — | 20000 | DMF | 10 | 100 | 67.3 |
| 46 | Pd(OAc)$_2$ | KBH$_4$, 50 eq | 20000 | DMF | 30 | 60.4 | 99.3 |
| 47 | Hydrogenation promoter(17) | KBH$_4$, 50 eq | 20000 | DMF | 10 | 99.8 | 99.3 |
| M | Hydrogenation promoter(18) | Bu$_4$NBH$_4$, 15 eq | 10000 | THF | 10 | 100 | 99.5 |
| N | Hydrogenation promoter(A) | Bu$_4$NBH$_4$, 2 eq | 20000 | THF | 2 | 100 | 96.2 |
| O | Hydrogenation promoter(C) | Bu$_4$NBH$_4$, 8.5 eq | 20000 | THF | 2 | 100 | 97.6 |
| P | Hydrogenation promoter(C) | Bu$_4$NBH$_4$, 20 eq | 20000 | THF | 3 | 100 | 98.1 |
| Q | Hydrogenation promoter(D) | Bu$_4$NBH$_4$, 15 eq | 10000 | THF | 30 | 100 | 99.8 |
| R | Hydrogenation promoter(E) | Bu$_4$NBH$_4$, 15 eq | 10000 | THF | 60 | 98.0 | 99.8 |
| S | Hydrogenation promoter(F) | Bu$_4$NBH$_4$, 15 eq | 10000 | THF | 10 | 100 | 99.6 |
| T | Hydrogenation promoter(G) | Bu$_4$NBH$_4$, 15 eq | 10000 | THF | 10 | 100 | 99.5 |
| U | Hydrogenation promoter(H) | Bu$_4$NBH$_4$, 15 eq | 10000 | THF | 30 | 100 | 99.8 |
| V | Hydrogenation promoter(I) | Bu$_4$NBH$_4$, 8.5 eq | 20000 | THF | 5 | 100 | 97.1 |
| W | Hydrogenation promoter(J) | Bu$_4$NBH$_4$, 8.5 eq | 20000 | THF | 30 | 100 | 97.6 |
| X | Hydrogenation promoter(K) | Bu$_4$NBH$_4$, 8.5 eq | 20000 | THF | 30 | 96.9 | 99.8 |

[X1] eq is an equivalent amount relative to Pd.

The comparison of Example 43, Example 44, and Example 47 suggested that the hydrogenation promoter (4) prepared by a reaction of Pd(OAc)$_2$, an alkyne, and a base, the hydrogenation promoter (18) prepared by a reaction of Pd(OAc)$_2$ and an alkynyl alcohol (without using the base), and the hydrogenation promoter (17) prepared by a reaction of Pd(OAc)$_2$ and the alkynyl alcohol (with the base) substantially had the which 4-octyne was hydrogenated in the presence of hydrogenation catalysts (1) to (5) and (L) of Examples 19 to 23 and L, respectively. The hydrogenation reaction was performed as in Example 24. However, in Examples 48 to 53 and AA, since a base or a reducing agent had been added during the preparation of the hydrogenation catalysts, a base or a reducing agent was not added during the hydrogenation reaction.

TABLE 6

| Example | Hydrogenation promoter or Hydrogenation catalyst | Base or Reducing agent[X1] | S/C | Solvent | Reaction time (min) | Conversion rate (%) | Selectivity (%) |
|---|---|---|---|---|---|---|---|
| 26 | Hydrogenation promoter(1) | $NaBH_4$, 50 eq | 20000 | DMF | 5 | 100 | 98.1 |
| 28 | Hydrogenation promoter(1) | $KBH_4$, 50 eq | 20000 | DMF | 5 | 99.9 | 98.7 |
| P | Hydrogenation promoter(C) | $Bu_4NBH_4$, 20 eq | 20000 | THF | 3 | 100 | 98.1 |
| 48 | Hydrogenation catalyst(1) | — | 20000 | DMF | 3 | 100 | 98.3 |
| 49 | Hydrogenation catalyst(1) | — | 20000 | DMF | 5 | 100 | 98.6 |
| 50 | Hydrogenation catalyst(2) | — | 20000 | DMF | 5 | 100 | 98.4 |
| 51 | Hydrogenation catalyst(3) | — | 20000 | DMF | 5 | 100 | 98.5 |
| 52 | Hydrogenation catalyst(4) | — | 20000 | DMF | 10 | 100 | 98.5 |
| 53 | Hydrogenation catalyst(5) | — | 20000 | DMF | 5 | 100 | 98.8 |
| AA | Hydrogenation catalyst(L) | — | 20000 | THF | 3 | 100 | 97.8 |

[X1] eq is an equivalent amount relative to Pd.

The comparison of Examples 48, 49, and AA with Examples 26, 28, and P showed that there was no significant difference between the case where the preparation of the hydrogenation catalyst was performed before hydrogenation reaction and the case where the preparation of the hydrogenation catalyst was performed during hydrogenation reaction, and similar hydrogenation catalysts were produced in both cases. The results of Examples 48 to 53 showed that when the preparation of the hydrogenation catalyst was performed before hydrogenation reaction, alkoxides having various structures could be used for preparing the hydrogenation promoter.

Examples 54 to 61

Table 7 shows the results of Examples 28 and 54 to 61. Examples 54 to 61 are reaction examples in which 4-octyne was hydrogenated in the presence of hydrogenation catalysts containing a divalent palladium compound, and a base or a reducing agent. The hydrogenation reaction in these examples was performed in accordance with Example 24.

Examples 54 to 58 show examples in which the divalent palladium compound is a dicationic complex. The comparison of Examples 54 to 58 with Example 28 showed that $[Pd(dmf)_4]^{2+}(2BF_4)^{2-}$ had a performance similar to that of the hydrogenation promoter (1). Examples 59 to 61 show examples in which the divalent palladium compound is a divalent neutral palladium compound. The comparison of Examples 59 to 61 with Example 28 showed that the hydrogenation catalysts containing a divalent neutral palladium compound and a base satisfactorily promoted hydrogenation reaction of an alkyne compound and provided a satisfactorily high cis-selectivity.

Examples 62 to 66

Table 8 shows the results of Examples 62 to 66. Examples 62 to 66 are reaction examples in which 4-octyne was hydrogenated in the presence of hydrogenation catalysts containing palladium (II) chloride and a base. The reaction substrate was 4-octyne, and the S/C ratio was controlled to 1,000. The hydrogenation reaction in these examples was performed in accordance with Example 24.

TABLE 7

| Example | Hydrogenation promoter and the like | Base or Reducing agent[X1] | S/C | Solvent | Reaction time (min) | Conversion rate (%) | Selectivity (%) |
|---|---|---|---|---|---|---|---|
| 28 | Hydrogenation promoter(1) | $KBH_4$, 50 eq | 20000 | DMF | 5 | 99.9 | 98.7 |
| 54 | $[Pd(dmf)_4]^{2+}(2BF_4)^{2-}$ | $KBH_4$, 50 eq | 20000 | DMF | 10 | 100 | 98.0 |
| 55 | $[Pd(dmf)_4]^{2+}(2BF_4)^{2-}$ | $Bu_4NBH_4$, 50 eq | 20000 | DMF | 30 | 99.8 | 98.8 |
| 56 | $[Pd(dmf)_4]^{2+}(2BF_4)^{2-}$ | $Bu_4NBH_4$, 50 eq | 20000 | THF | 30 | 100 | 97.8 |
| 57 | $[Pd(dmf)_4]^{2+}(2BF_4)^{2-}$ | $Bu_4NBH_4$, 50 eq | 20000 | tBuOH | 5 | 100 | 93.1 |
| 58 | $[Pd(dmf)_4]^{2+}(2BF_4)^{2-}$ | KOtBu, 50 eq | 20000 | tBuOH | 30 | 100 | 96.5 |
| 59 | $PdCl_2$ | KOtBu, 50 eq | 1000 | DMF + IPA[X2] | 7 | 100 | 99.0 |
| 60 | $Pd(NO_3)_2$ | KOtBu, 50 eq | 1000 | DMF + IPA[X2] | 7 | 98.5 | 98.2 |
| 61 | $PdCl_2(CH_3CN)_2$ | KOtBu, 12 eq | 1000 | IPA | 60 | 100 | 94.0 |

[X1] eq is an equivalent amount relative to Pd.
[X2] A mixed solvent of DMF:IPA = 4:1 was used as DMF + IPA

TABLE 8

| Example | Divalent neutral palladium | Base or Reducing agent[X1] | Addition | Solvent | Reaction time (min) | Conversion rate (%) | Selectivity (%) |
|---|---|---|---|---|---|---|---|
| 62 | $PdCl_2$ | KOtBu, 50 eq | — | DMF + tBuOH[X2] | 7 | 100 | 99.0 |
| 63 | $PdCl_2$ | KOtBu, 50 eq | 18-crown-6 | DMF + tBuOH[X2] | 14 | 100 | 99.6 |
| 64 | $PdCl_2$ | KOtBu, 50 eq | cryptand | DMF + tBuOH[X2] | 11 | 100 | 99.9 |

TABLE 8-continued

| Example | Divalent neutral palladium | Base or Reducing agent[X1] | Addition | Solvent | Reaction time (min) | Conversion rate (%) | Selectivity (%) |
|---|---|---|---|---|---|---|---|
| 65 | $PdCl_2$ | NaOtBu, 100 eq | — | DMF + tBuOH[X2] | 7 | 96.0 | 99.5 |
| 66 | $PdCl_2$ | NaOtBu, 100 eq | 15-crown-5 | DMF + tBuOH[X2] | 40 | 99.8 | 99.8 |

[X1] eq is an equivalent amount relative to Pd.
[X2] A mixed solvent of DMF:tBuOH = 19:1 was used as DMF + tBuOH Examples 63, 64, and 66 are examples in which a host compound was added as an additive in an amount of 100 equivalents relative to Pd. The comparison of Examples 63 and 64 with Example 62 and the comparison of Example 65 with Example 66 showed that the selectivity tended to improve with the addition of the host compound.

Examples 67 to 70

Table 9 shows the results of Examples 26 to 29 and 67 to 70. Examples 67 to 70 are examples in which 4-octyne was hydrogenated under various conditions. The hydrogenation reaction in these examples was performed in accordance with Example 24.

The hydrogenation reaction in these examples was performed in accordance with Example 24. The reaction substrates were purified with a base and $Bu_4NBH_4$ to remove acidic substances, ketones, and the like, and then used. A typical purification method will be described in Example 80.

Example 80

4-Octyne containing 0.46% of an acetylenic ketone as an impurity was purified as follows. First, 40 mL (273 mmol) of 4-octyne was fed in a separatory funnel and washed with a 1% $Na_2CO_3$ aqueous solution (10 mL×5 times) to neutralize an acidic component. The liquid was washed with water and a saturated aqueous NaCl solution, and dried over 1.5 g of

TABLE 9

| Example | Hydrogenation promoter | Base or Reducing agent[X1] | S/C | Solvent | Reaction time (min) | Conversion rate (%) | Selectivity (%) |
|---|---|---|---|---|---|---|---|
| 26 | Hydrogenation promoter(1) | $NaBH_4$, 50 eq | 20000 | DMF | 5 | 100 | 98.1 |
| 27 | Hydrogenation promoter(1) | $KBH_4$, 50 eq | 20000 | DMF | 5 | 99.9 | 98.7 |
| 28 | Hydrogenation promoter(1) | KOtBu, 50 eq | 20000 | DMF | 5 | 100 | 96.4 |
| 29 | Hydrogenation promoter(1) | — | 20000 | DMF | 10 | 100 | 56.2 |
| 67 | Hydrogenation promoter(1) | $Bu_4NBH_4$, 50 eq | 20000 | DMF | 3 | 100 | 98.0 |
| 68 | Hydrogenation promoter(1) | $Bu_4NBH_4$, 50 eq | 20000 | DMA | 10 | 100 | 98.0 |
| 69 | Hydrogenation promoter(1) | $Bu_4NBH_4$, 50 eq | 20000 | THF | 10 | 100 | 99.5 |
| 70 | Hydrogenation promoter(1) | $Bu_4NBH_4$, 50 eq | 20000 | tBuOH | 30 | 100 | 98.5 |

[X1] eq is an equivalent amount relative to Pd.

In Examples 26 to 29 and Examples 67 to 70, the effect of the type of base or reducing agent and type of solvent on the hydrogenation performance was examined when the hydrogenation promoter (1) was used. According to the comparison of these examples, when a base or a reducing agent was used in hydrogenation reaction, very high numerical values of both the conversion rate and the cis-selectivity were achieved, compared with the case where neither a base nor a reducing agent was used in hydrogenation reaction (Example 29). Furthermore, in hydrogenation reaction, the use of a reducing agent tended to provide a satisfactory cis-selectivity, compared with the case where a base was used.

Examples 71 to 79

Table 10 shows the results of Examples 71 to 79. Examples 71 to 79 are hydrogenation reaction examples of various types of reaction substrate. The hydrogenation promoter (1) was used, and a reducing agent was added during hydrogenation reaction to prepare a hydrogenation catalyst in the system.

anhydrous $Na_2SO_4$. The treated 4-octyne was transferred into a 100-mL eggplant-type flask. Subsequently, 1.40 g (5.46 mmol) of $Bu_4NBH_4$ was added to the flask, and the mixture was stirred. The solubility of $Bu_4NBH_4$ in 4-octyne was low, and thus $Bu_4NBH_4$ was suspended in the form of a white powder even under stirring. However, heat generation and a change in the color tone were observed within a few minutes, and a reaction between the acetylenic ketone and $Bu_4NBH_4$ was initiated. After the mixture was stirred at 50° C. for one hour, a reaction product of the acetylenic ketone and $Bu_4NBH_4$ was obtained as a viscous liquid. The viscous liquid was separated from 4-octyne, 1.40 g (5.46 mmol) of Bu4NBH4 was added to 4-octyne again, and the mixture was stirred at 50° C. for one hour. Subsequently, $Bu_4NBH_4$ was removed by filtration, and the liquid was then washed with water to remove any trace amount of $Bu_4NBH_4$ dissolved in 4-octyne. The liquid was washed with a saturated aqueous NaCl solution, and then distilled under a reduced pressure to prepare 4-octyne. In the GC analysis of 4-octyne purified by this process, the acetylenic ketone was not detected.

TABLE 10

| Example | Substrate | Used amount of $Bu_4NBH_4$[X2] | S/C | Solvent | Reaction time (min) | Conversion rate (%) | Selectivity (%) |
|---|---|---|---|---|---|---|---|
| 71 | 4-octyne[X1] | 10 eq | 20000 | THF | 3 | 100 | 96.0 |
| 72 | 4-octyne | 10 eq | 20000 | THF | 10 | 99.4 | 99.5 |
| 73 | diphenylacetylene | 10 eq | 20000 | THF | 10 | 100 | 97.1 |
| 74 | bis(trimethylsilyl)acetylene | 1 eq | 1000 | THF | 120 | 43.0 | 77.5 |
| 75 | 1-trymethylsilyl-1-hexyne | 10 eq | 20000 | THF | 120 | 100 | 92.4 |
| 76 | 3-hexyne-1-ol | 25 eq | 20000 | THF | 5 | 100 | 99.5 |
| 77 | 10-chloro-3-decyne | 25 eq | 20000 | THF | 10 | 100 | 96.9 |
| 78 | 1-pentyn | 200 eq | 20000 | THF | 30 | 100 | 97.0[X3] |
| 79 | phenylacetylene | 200 eq | 20000 | THF | 120 | 100 | 95.9[X3] |

[X1]Substrate containing 0.46% of an acetylenic ketone, without performing substrate reduction according to Example 82
[X2]eq is an equivalent amount relative to Pd.
[X3]The ratio of a terminal alkene on the sum of all the amount of alkenes (terminal alkene + internal alkene) and alkanes.

Examples 71 to 77 are hydrogenation reaction examples of internal alkynes, and Examples 78 and 79 are hydrogenation reaction examples of terminal alkynes. The results showed that the internal alkynes and the terminal alkynes were efficiently hydrogenated to alkene compounds. According to the results of Examples 74 to 77, hydrogenation of substrates having a trimethylsilyl (TMS) group, a hydroxyl group, or a halogen as a substituent also satisfactorily proceeded, showing a wide application of the hydrogenation catalyst of the present invention. The result of Example 73 showed that, in hydrogenation of a substrate having relatively bulky groups, such as phenyl groups, at both ends of the triple bond, a cis-alkene could be produced with a high efficiency. According to the result of Example 74, in a substrate having very bulky groups, such as trimethylsilyl groups, at both ends of the triple bond, although the activity was somewhat low, hydrogenation reaction proceeded when the S/C ratio was set to a low value. The results of Examples 78 and 79 showed that hydrogenation reaction from a compound having a triple bond at a terminal to a compound having a double bond at the terminal proceeded with a high yield and a high selectivity.

Examples AB to AV and Examples BA to BN

Table 11 shows the results of Examples AB to AI, AJ to AP, and AQ to AV. These examples are hydrogenation reaction examples of internal alkynes using various types of hydrogenation promoter. In Examples AB to AI, 4-octyne was used as the reaction substrate. In Examples AJ to AP, 1-phenyl-1-butyne was used as the reaction substrate. In Examples AQ to AV, diphenylacetylene was used as the reaction substrate. The hydrogenation reaction in these examples was performed in accordance with Example 24. Comparative Examples A, B, and C are hydrogenation reaction examples using a Lindlar catalyst, and 4-octyne, 1-phenyl-1-butyne, and diphenylacetylene were used as the reaction substrate, respectively. In these comparative examples, $Bu_4NBH_4$ was not added, and quinoline was added. The hydrogenation reaction in these examples was performed in accordance with Example 24.

Table 12 shows the results of Examples BA to BG and BH to BN. These examples are hydrogenation reaction examples of terminal alkynes using various types of hydrogenation promoter. In Examples BA to BG, 1-pentyne was used as the reaction substrate. In Examples BH to BN, phenylacetylene was used as the reaction substrate. The hydrogenation reaction in these examples was performed in accordance with Example 24. Comparative Examples D and E are hydrogenation reaction examples using the Lindlar catalyst, and 1-pentyne and phenylacetylene were used as the reaction substrate, respectively. In these comparative examples, $BU_4NBH_4$ was not added, and quinoline was added.

TABLE 11

| Example or Comparative Example | Substrate | Hydrogenation promoter or Hydrogenation catalyst | Used amount of $Bu_4NBH_4$[X1] | Reaction time (min)[X2] | Conversion rate (%) | Selectivity (%) |
|---|---|---|---|---|---|---|
| Example AB | 4-octyne | Hydrogenation promoter(4) | 15 eq | 10 min | 99.9 | 99.8 |
| Example AC | 4-octyne | Hydrogenation promoter(G) | 15 eq | 10 min | 100 | 99.5 |
| Example AD | 4-octyne | Hydrogenation promoter(F) | 15 eq | 10 min | 100 | 99.6 |
| Example AE | 4-octyne | Hydrogenation promoter(D) | 15 eq | 30 min | 100 | 99.8 |
| Example AF | 4-octyne | Hydrogenation promoter(E) | 15 eq | 60 min | 98.0 | 99.8 |
| Example AG | 4-octyne | Hydrogenation promoter(18) | 15 eq | 60 min | 99.4 | 99.7 |
| Example AH | 4-octyne | Hydrogenation promoter(H) | 15 eq | 60 min | 88.6 | 99.6 |
| Example AI | 4-octyne | Hydrogenation promoter | 10 eq | 30 min | 99.8 | 97.9 |
| Comparative Example A | 4-octyne | Lindlar catalyst | 10000 eq[X3] | 240 min | 99.5 | 96.9 |

TABLE 11-continued

| Example or Comparative Example | Substrate | Hydrogenation promoter or Hydrogenation catalyst | Used amount of $Bu_4NBH_4$ [X.1] | Reaction time (min) [X.2] | Conversion rate (%) | Selectivity (%) |
|---|---|---|---|---|---|---|
| Example AJ | 1-phenyl-1-butyne | Hydrogenation promoter(4) | 15 eq | 5 min | 100 | 79.1 |
| Example AK | 1-phenyl-1-butyne | Hydrogenation promoter(G) | 15 eq | 10 min | 99.9 | 69.9 |
| Example AL | 1-phenyl-1-butyne | Hydrogenation promoter(F) | 15 eq | 10 min | 100 | 66.6 |
| Example AM | 1-phenyl-1-butyne | Hydrogenation promoter(D) | 15 eq | 10 min | 100 | 76.4 |
| Example AN | 1-phenyl-1-butyne | Hydrogenation promoter(E) | 15 eq | 5 min | 100 | 93.2 |
| Example AO | 1-phenyl-1-butyne | Hydrogenation promoter(18) | 15 eq | 60 min | 100 | 98.6 |
| Example AP | 1-phenyl-1-butyne | Hydrogenation promoter(H) | 15 eq | 10 min | 100 | 90.5 |
| Comparative Example B | 1-phenyl-1-butyne | Lindlar catalyst | 10000 eq [X.3] | 120 min | 100 | 91.1 |
| Example AQ | diphenylacetylene | Hydrogenation promoter(4) | 15 eq | 60 min | 100 | 98.0 |
| Example AR | diphenylacetylene | Hydrogenation promoter(G) | 15 eq | 30 min | 100 | 96.5 |
| Example AS | diphenylacetylene | Hydrogenation promoter(F) | 15 eq | 60 min | 100 | 96.0 |
| Example AT | diphenylacetylene | Hydrogenation promoter(D) | 15 eq | 10 min | 100 | 96.9 |
| Example AU | diphenylacetylene | Hydrogenation promoter(E) | 15 eq | 60 min | 100 | 98.0 |
| Example AV | diphenylacetylene | Hydrogenation promoter(18) | 15 eq | 180 min | 100 | 97.3 |
| Comparative Example C | diphenylacetylene | Lindlar catalyst | 10000 eq [X.3] | 600 min | 46.5 | 96.8 |

[X.1] eq is an equivalent amount relative to Pd
[X.2] In Example AB to AH and Comparative Example A, S/C was 10000, and a reaction solvent was THF.
[X.3] Used amount of quinoline
[X.4] Palladium nanoparticles that contained polyvinylpyrropidone(PVP) as an agglomeration-preventing agent was used as a hydrogenation promoter. This nanoparticles is prepared using $Pd(OAc)_2$ as Pd compound. KOtBu as a base. and PVP instead of alkyne compound.

TABLE 12

| Example or Comparative Example | Substrate | Hydrogenation promoter or Hydrogenation catalyst | Used amount of $Bu_4NBH_4$ [X.1] | Reaction time (min) [X.2] | Conversion rate (%) | Selectivity (%) |
|---|---|---|---|---|---|---|
| Example BA | 1-pentyne | Hydrogenation promoter(4) | 200 eq | 30 min | 100 | 95.2 |
| Example BB | 1-pentyne | Hydrogenation promoter(G) | 200 eq | 30 min | 100 | 89.4 |
| Example BC | 1-pentyne | Hydrogenation promoter(F) | 200 eq | 30 min | 100 | 94.0 |
| Example BD | 1-pentyne | Hydrogenation promoter(D) | 200 eq | 10 min | 100 | 95.1 |
| Example BE | 1-pentyne | Hydrogenation promoter(E) | 200 eq | 10 min | 100 | 95.5 |
| Example BF | 1-pentyne | Hydrogenation promoter(18) | 200 eq | 10 min | 100 | 94.0 |
| Example BG | 1-pentyne | Hydrogenation promoter(H) | 200 eq | 5 min | 100 | 96.0 |
| Comparative Example D | 1-pentyne | Lindlar catalyst | 10000 eq | 75 min | 100 | 96.0 |
| Example BH | phenylacetylene | Hydrogenation promoter(4) | 200 eq | 30 min | 100 | 93.7 |
| Example BI | phenylacetylene | Hydrogenation promoter(G) | 200 eq | 60 min | 73.2 | 96.8 |
| Example BJ | phenylacetylene | Hydrogenation promoter(F) | 200 eq | 60 min | 96.5 | 95.2 |
| Example BK | phenylacetylene | Hydrogenation promoter(D) | 200 eq | 30 min | 100 | 90.3 |
| Example BL | phenylacetylene | Hydrogenation promoter(E) | 200 eq | 30 min | 100 | 93.9 |
| Example BM | phenylacetylene | Hydrogenation promoter(18) | 200 eq | 10 min | 100 | 93.9 |
| Example BN | phenylacetylene | Hydrogenation promoter(H) | 200 eq | 5 min | 100 | 96.0 |
| Comparative Example E | phenylacetylene | Lindlar catalyst | 10000 eq | 15 min | 100 | 84.5 |

[X.1] eq is an equivalent amount relative to Pd
[X.2] In Example AB to AH and Comparative Example A, S/C was 10000 and a reaction solvent was THF
[X.3] Used amount of quinoline The results of Examples AB to AI, AJ to AP, AQ to AV, BA to BG, and BH to BN showed that a hydrogenation promoter exhibiting a high activity differed according to the structure of the reaction substrate.

For example, when the reaction substrate was 4-octyne, although the conversion rate in the reaction with the hydrogenation promoter (H) tended to be somewhat low, other hydrogenation promoters provided satisfactory conversion rates, and all the hydrogenation promoters provided satisfactory values of selectivity. In addition, when (known) palladium nanoparticles that contained polyvinylpyrrolidone (PVP) as an agglomeration-preventing agent, and a borohydride compound were used, satisfactory results were obtained (Example AI).

When the reaction substrate was 1-phenyl-1-butyne in which excessive hydrogenation reaction producing an alkane easily proceeds, all the hydrogenation promoters provided satisfactory conversion rates, but the hydrogenation promoters (E) and (18) particularly provided satisfactory values of selectivity. When the reaction substrate was diphenylacetylene, all the hydrogenation promoters provided satisfactory conversion rates and satisfactory values of selectivity.

When the reaction substrate was 1-pentyne, all the hydrogenation promoters provided satisfactory conversion rates, but the hydrogenation promoters (D), (E), (18), and (H) particularly provided high conversion rates within a short time. Although the selectivity in the reaction with the hydrogenation promoter (G) tended to be somewhat low, other hydrogenation promoters provided satisfactory values of selectivity.

When the reaction substrate was phenylacetylene, although the conversion rate in the reaction with the hydrogenation promoter (G) tended to be somewhat low, other hydrogenation promoters provided satisfactory conversion rates, and the hydrogenation promoters (18) and (H) particularly provided high conversion rates within a short time. Although the selectivity in the reaction with the hydrogenation promoter (D) tended to be somewhat low, other hydrogenation promoters provided satisfactory values of selectivity.

Additionally, referring to the results of Comparative Examples A to E, the hydrogenation promoters and the hydrogenation catalysts according to the present invention have excellent activity and selectivity compared with the Lindlar catalyst, which is a known catalyst system. In particular, it is difficult to conduct hydrogenation of bulky reaction substrates, such as diphenylacetylene, with the Lindlar catalyst, but such a hydrogenation reaction efficiently proceeds in the catalyst system described in this patent.

Examples 81 and 82

Table 13 shows the results of Examples 81 and 82. Example 82 is an example in which hydrogenation reaction was conducted after a hydrogenation catalyst was treated with hydrogen gas in advance. The hydrogenation promoter (1) was used, and a reducing agent was added during the hydrogenation reaction to prepare the hydrogenation catalyst. The hydrogenation reaction was conducted under a condition of S/C=20,000. The hydrogenation reaction in these examples was performed in accordance with Example 24.

TABLE 13

| Example | Substrate | Reducing agent[X1] | Solvent | Pretreatment time (min) | Reaction time (hr) | Conversion rate (%) | Selectivity (%) |
|---|---|---|---|---|---|---|---|
| 81 | 1-pentyne | $KBH_4$, 2000 eq | DMF | 0 | 2.5 | 99.2 | 98.3 |
| 82 | 1-pentyne | $KBH_4$, 2000 eq | DMF | 30 | 1 | 100 | 99.4 |

[X1] eq is an equivalent amount relative to Pd

According to the comparison of Example 81 with Example 82, by performing the hydrogen treatment of the hydrogenation catalyst in advance, the activity of the hydrogenation catalyst tended to improve.

Examples 83 to 85 and Comparative Examples 1 and 2

Table 14 shows the results of Examples 67, 48, and 83 to 85, and Comparative Examples 1 and 2. Examples 83 to 85 are examples in which 4-octyne was hydrogenated under a condition of a high S/C ratio. The hydrogenation reaction in these examples was performed in accordance with Example 24.

TABLE 14

| | Hydrogenation promoter or Hydrogenation catalyst | Base or Reducing agent (eq)[X1] | S/C | Solvent | Reaction time | above: Conversion rate % below: Selectivity % | TON (×10⁴) | TOF (sec⁻¹) |
|---|---|---|---|---|---|---|---|---|
| Example | | | | | | | | |
| 67 | Hydrogenation promoter(1) | $Bu_4NBH_4$ (50 eq) | 20000 | DMF | 3 min | 100 / 98.0 | 2.00 | 111 |

TABLE 14-continued

| | Hydrogenation promoter or Hydrogenation catalyst | Base or Reducing agent (eq)[X1] | S/C | Solvent | Reaction time | above: Conversion rate % below: Selectivity % | TON (×10⁴) | TOF (sec⁻¹) |
|---|---|---|---|---|---|---|---|---|
| 48 | Hydrogenation catalyst(1) | — | 20000 | DMF | 3 min | 100 / 98.3 | 2.00 | 111 |
| 83 | Hydrogenation promoter(1) | KBH₄ (200 eq) | 100000 | DMF | 10 min | 99.9 / 98.8 | 10.0 | 167 |
| 84 | Hydrogenation promoter(1) | LiBH₄ (20200 eq) | 1030000 | DMF | 48 h | 99.5 / 99.7 | 103 | 5.9 |
| 85 | Hydrogenation promoter(1) | LiBH₄ (330000 eq) | 11000000 | DMF | 216 h | 76.5 / 99.9 | 842 | 10.8 |
| Comparative Example | | | | | | | | |
| 1 | Lindlar catalyst | quinoline (5000 eq) | 100000 | MeOH | 10 min | 2.9 / 97.3 | 0.29 | 4.8 |
| 2 | Caubere catalyst | quinoline (5000 eq) | 100000 | EtOH | 10 min | <7.7 / 97.7 | 0.77 | 12.8 |

[X1]eq is an equivalent amount relative to Pd

Examples 67, 48, and 83 to 85 had extremely high activities compared with Comparative Example 1 in which the Lindlar catalyst was used and Comparative Example 2 in which a Caubere catalyst was used. The cis-selectivity and the TON of these examples also surpassed those of the comparative examples. In Example 83, when the hydrogenation promoter (1) was used as a component of a hydrogenation catalyst even under a condition of S/C=100,000, hydrogenation reaction proceeded within 10 minutes, and the TOF reached 167 sec⁻¹. In Example 85, when the hydrogenation promoter (1) was used as a component of a hydrogenation catalyst under a condition of S/C=11,000,000, the TON reached 841.5×10⁴.

INDUSTRIAL APPLICABILITY

The present invention can be mainly used in the chemical industry and, for example, used in the production of various cis-alkenes used as intermediates of medicines or agricultural chemicals.

The invention claimed is:

1. A process for producing a cis-alkene compound comprising partially hydrogenating an internal alkyne compound, which is a reaction substrate, using a hydrogenation catalyst in a solvent in the presence of hydrogen, or a compound that provides hydrogen, thereby yielding the cis-alkene compound with high selectivity, wherein the hydrogenation catalyst comprises at least one of a base and a reducing agent; and a hydrogenation promoter produced by reacting a compound selected from the group consisting of an alkyne compound, an alkene compound, an alkynyl alcohol compound, and an alkenyl alcohol compound;

at least one palladium compound selected from the group consisting of palladium compounds represented by general formulae (1) to (4) or at least one multimer thereof, $$Pd(II)X_jL_k \quad (1)$$

$$\text{a salt of } (Pd(II)X_m)^{2-} \quad (2)$$

$$\text{a salt of } (Pd(II)L_n)^{2+} \quad (3)$$

$$\text{a salt of } (Pd(IV)X_p)^{2-} \quad (4)$$

wherein each L, independently, represents a monodentate ligand or a polydendate ligand other than a phosphorus-containing ligand, X represents an anionic group, j represents a value determined according to the valence of X so that $X_j$ has a valence of −2 as a whole, k represents an integer of from 0 to 4, m represents a value determined according to the valence of X so that $X_m$ has a valence of −4 as a whole, n represents an integer of from 4 to 6, and p represents a value determined according to the valence of X so that $X_p$ has a valence of −6 as a whole; and a base, in an organic solvent.

2. The method for producing a cis-alkene compound according to claim 1, wherein the hydrogenation promoter comprises palladium nanoparticles containing the alkyne compound, the alkene compound, the alkynyl alcohol compound, or the alkenyl alcohol compound, as an agglomeration-preventing agent.

3. The process for producing a cis-alkene compound according to claim 1, wherein the reducing agent is a borohydride compound.

4. The process for producing a cis-alkene compound according to claim 1, wherein the hydrogenation reaction of the alkyne compound is conducted after the hydrogenation catalyst is treated with hydrogen gas in advance.

* * * * *